United States Patent [19]
Feke et al.

[11] Patent Number: 5,830,147
[45] Date of Patent: Nov. 3, 1998

[54] METHOD AND APPARATUS FOR EXAMINING OPTIC NERVE HEAD CIRCULATION

[75] Inventors: Gilbert T. Feke; Gilbert D. Feke, both of Stoneham, Mass.

[73] Assignee: Schepens Eye Research Institute, Inc., Boston, Mass.

[21] Appl. No.: 866,539

[22] Filed: May 30, 1997

[51] Int. Cl.$^6$ ..................................................... A61B 5/02
[52] U.S. Cl. .......................... 600/479; 600/504; 600/558; 351/221; 351/246
[58] Field of Search ..................................... 600/479, 504, 600/558; 356/28; 351/205, 221, 246

[56] References Cited

U.S. PATENT DOCUMENTS

| | | | |
|---|---|---|---|
| 4,109,647 | 8/1978 | Stern et al. | 600/479 |
| 5,106,184 | 4/1992 | Milbocker | 351/221 |
| 5,615,683 | 4/1997 | Toge et al. | 600/479 |
| 5,620,000 | 4/1997 | Zinser et al. | 600/479 |

OTHER PUBLICATIONS

Riva, C.E. et al. (1975) "Blood Flow in Capillaries of the Optic Nerve" *European Society of Ophthalmology* pp. 412–416.

Bonner, R.F. et al. "Principles of Laser–Doppler Flowmetry" in Shepherd AP, Oberg PA (eds) Laser Doppler Blood Flowmetry, Boston, Kluwer Academic Pub. 1990 pp. 17–45.

Petrig, B.L. et al. (1996) "Optic Nerve Head Laser Doppler Flowmetry: Principles and Computer Analysis" *Petrig/Riva* pp. 120–127.

Sebag, J. et al. (1986) "Anterior Optic Nerve Blood Flow Decreases in Clinical Neurogenic Optic Atropy" *Ophthalmology*, Vol. 93, No. 6, pp. 858–865.

Riva, C.E. et al. (1989) "Noninvasive Measurement of the Optic Nerve Head Circulation" pp. 129–136.

(List continued on next page.)

*Primary Examiner*—Ruth S. Smith
*Attorney, Agent, or Firm*—Lahive & Cockfield, LLP

[57] ABSTRACT

A laser source attached to an ophthalmic observation instrument, such as a fundus camera, projects a spot, and a light collector is positioned in the image field of the instrument over the spot to collect return light scattered from a homogeneous tissue bed in the image field. The collected light is directed onto a photomultiplier and digitized at a sampling rate above several kHz to provide a continuous data stream which is fed to a process/control module that operates to automatically define a number n of sample intervals, select a subset of the sample intervals for analysis, transform the selected intervals, and evaluate the shape of the transformed sample intervals. The process/control module may be implemented on a simple computer, and include a user interface which indicates status of signal acquisition, selection and evaluation during a short, e.g., one-minute illumination interval. The ophthalmic instrument images tissue of the fundus, and the light collector is configured to collect light from a target region having a diameter under 0.5 mm, preferably under 0.2 mm, and as little as 0.02 mm which is selected by the operator by moving the light collector to a region of the image field which corresponds to the illumination spot, and is free of vessels. The control/analysis module also receives patient data via keyboard or network communication, and merges patient data with the acquired spectra to form medical records. Preferably, it also accesses or files records for the same patient in storage. A number of threshold, evaluation or diagnostic routines are implemented as macros to highlight or annotate the transformed measurement spectra and display the annotated data. The module is set to carry out signal acquisition for no more than a fixed number n of one-second intervals, and to terminate acquisition earlier if it has evaluated and positively approved a second, lesser fixed number m of well-formed signal traces. Audible prompts indicate acquisition of proper traces, and completion of analysis or fitting steps. A printer may print out spectra and derived data with user-entered annotations.

12 Claims, 8 Drawing Sheets

OTHER PUBLICATIONS

Rizzo, J.F. (1991) "Optic Nerve Head Blood Speed as a Function of Age in Normal Human Subjects" *Investigative Ophthalmolog & Visual Science*, vol. 32, No. 13 pp. 3263–3272.

Sebag, J. et al. (1985) "Anterior Optic Nerve Blood Flow in Experimental Optic Arrophy" *Invest Ophthalmol Vis Sci* 26:1415–1422.

Feke, G. T. et al. (1995), *British Journal of Ophthalmology* 79:5088–1092.

Riva, C. E. (1982) "Kaser Dopler Measurement of Relative Blood Velocity in the Human Optic Nerve Head" *Invest. Ophthalmol. Vis. Sci.* 22:241–248.

Netland, P. A. (996) "Optic Nerve Head Circulation After Topical Calcium Channel Blocker" *Journal of Glaucoma* 5:200–206.

METHOD AND APPARATUS FOR EXAMINING OPTIC NERVE HEAD CIRCULATION

BACKGROUND

The present invention relates to methods and devices for evaluating tissue in the head of the optic nerve. This tissue consists of a tract of the central nervous system which joins the eyeball just medial to its posterior pole. The central artery to the retina runs through the sheath of the optic nerve, then branches out at the surface to supply the retina, so several small vessels are visible branching out centrally on its surface. The head itself, however is densely supplied by capillaries and presents a generally uniform, pale-colored diffusely perfused tissue bed. A number of aging or disease states are associated with changing color and atrophy of the optic nerve, and for a long time such changes were thought to occur due to impaired blood flow; for several conditions, ocular hypertension was believed to be responsible for the hypothesized flow impairment. More recently, it has become possible to evaluate parameters, such as blood speed in the capillary bed, that while not directly measuring blood flow, allow comparative estimates to be made of the adequacy of blood supply. By observing such parameters in the optic head and making comparative observations in patients with conditions such as low pressure glaucoma, it has become clear that a simple pressure/circulation etiology is unduly simplistic. However, whatever the causative mechanism of the studied disease states, the extent of capillary perfusion would be a valuable parameter to measure, both to provide some indication of tissue health, and because knowledge of this parameter may provide clues useful to understanding the dynamics of or changes occurring in, surrounding systems.

In general, laser Doppler techniques have proven valuable for blood flow measurements. When a directed flow has a large number of red cells, as occurs in blood vessels, coherent light of a wavelength reflected by red blood cells can be directed at a vessel and the light reflected back by the cells in the vessel can be collected, converted to an electrical signal by a photodiode, and the detected signal converted to a frequency histogram by Fourier transformation to yield a direct measure of the blood speed, or distribution of blood speeds, in the vessel. As described in U.S. Pat. No. 5,106,184, when this technique is applied to small retinal vessels, the diameter of the target vessel may be measured so that, together with a simple model of flow profile, it provides a basis for directly calculating the actual flow volume or rate. However, when blood is not flowing in a single oriented vessel, Doppler analysis is not so straightforward.

In the head of the optic nerve, where blood is supplied to the tissue from an underlying depth, the blood flow is almost entirely within capillaries distributed throughout the tissue. These capillaries form a filamentous network extending in all directions, so that the scattering of light by blood cells is a scattering by objects which may move in random directions, but which have similar characteristic velocities. Furthermore, under these conditions, photons directed at the tissue may undergo reflection or scattering from the stationary substrate, undergo scattering from one particle, or undergo multiple scattering events from multiple particles. In these circumstances, both the direction of particle movement and the direction of propagation of the scattered light are randomized. The number of blood cell-photon interactions will depend on factors such as the path length in tissue, average capillary size and spacing, degree of capillary development, blood cell density, and similar factors. In general, the amplitude of scattered light may also vary based on a number of conditions of blood composition, cellular health, tissue absorption characteristics and the like, and the overall form of the Doppler shifted spectrum obtained from a monochromatic source illumination may in theory also further depend on such features as the degree of isotropy of the photon-cell scattering event.

Taking a number of these factors into account, Stern and Lappe, assuming isotropic scattering and further assuming that blood speed in capillaries is effectively constant, developed a model to derive the shape of the frequency-transformed detected signal from light reflected by an organ, as described in U.S. Pat. No. 4,109,647. Aspects of this theory have been applied by applicant and others to the problem of remote measurements in the head of the optic nerve. More recently, Bonner and Nossal have put forth a somewhat more general theory which takes into account functional variables such as the mean number of scattering events per photon, and which varies these assumptions slightly and explores the implications of the propagation characteristics, a Gaussian speed distribution, an anisotropic scattering section and the path length. In general, the actual RBC cross-section in a capillary bed is low, about one to three per cent, so the frequency portion of the Doppler spectrum due to such blood scattering is dominated by single-event scattering and the probable blood speed can be deduced from it. However, the quantity of blood is not as easily determined owing to its small overall presence and the relatively large contributions and variations in other scattering and absorbance effects.

Several researchers and groups associated with the Scheie Eye Institute in Philadelphia or with a group in Heidelberg, respectively, have relied extensively on the Bonner and Nossal analysis and sought to directly model a flow measurement from the collected light and processed frequency spectra. In each of these models, a statistical model of scattering interactions is shown under some assumptions to imply that a function of the transformed frequencies will yield the blood flow. Overall, applying the Stem and Lappe approach, an estimate of particle speed may be derived which under reasonable assumptions is relatively independent of the blood volume present in the illuminated tissue. While other processing of collected light may provide additional data on which to base flow estimates, the complex functional dependence of the light interaction makes it difficult to model such quantities with assurance. Historically, a two instrument approach has also been applied to estimate blood flow in the head of the optic nerve, using reflectometry to determine the amount of circulating blood, and a Doppler method to derive the blood speed.

A simple inspection of unit scales will reveal that laser Doppler analysis (as contrasted to ultrasound Doppler analysis) should be able to resolve velocities typical of capillary flow, which are several orders of magnitude lower than vascular flow velocities. However, in practice there is great point-to-point variation in the nature of the collected signal, even in substantially identical tissues, and the interaction of scattering and absorption phenoma is sufficiently complex that even the selection of a few apparently plausible assumptions as a basis for modeling a total flow is likely to produce a highly speculative measure. This is especially true because of the dependence of many modeled parameters on the mean number of RBC scattering events, the relatively low RBC cross-section in capillary-supplied tissue and the relatively uncontrolled integration space which occurs when collecting from brightly lit small patches of tissue. In practice, even for simple determinations, research has involved collecting many signal traces; each is processed according to the specified analysis protocol and then may be inspected to determine whether is has produced a credible result, or should be discarded as having a measurement error, before inclusion in a data base. Such a procedure is ill-suited to clinical use where a specialist or instrument technician may lack the means for discriminating between a true measurement, and a false reading that results from unrelated local or global features of tissue absorbance and scattering effects, or from entirely unrelated physiological processes.

Accordingly, it would be desirable to produce a clinical instrument that reliably and accurately provides a repeatable and stable measure of capillary blood circulation in tissue.

It would be particularly desirable to produce such an instrument adapted for measurement of blood speed in the optic nerve head.

It would further be desirable to provide such an instrument which is removably or incrementally attachable to a standard ophthalmic examination instrument, and which allows a clinician to augment information obtained in a single examination, without switching instruments or having to correlate different visual fields.

SUMMARY OF THE INVENTION

The present invention solves the foregoing problems and achieves one or more of these desired ends by providing a laser source attached to an ophthalmic observation instrument, such as a fundus camera, to project a spot of light into the head of the optic nerve, and a light collector positionable in the image field of the instrument to collect return light scattered from a homogeneous tissue bed in the image field. The collected light is directed onto a photomultiplier and digitized at a sampling rate above several kHz to provide a continuous data stream which is fed to a process/control module that defines a number m of sample intervals, selects a subset of the sample intervals for analysis, transforms the selected intervals, and evaluates the shape of the transformed sample intervals.

The process/control module may be implemented on a simple computer, and preferably includes a user interface which indicates status of signal acquisition, selection and evaluation during a short, e.g., one or two minute, patient illumination and signal acquisition interval.

Preferably, the ophthalmic instrument is a fundus imaging instrument, and the light collector is sized to collect light from a target region having a diameter under 0.5 mm, most preferably under 0.2 mm, and for some applications in the range of 0.02 to 0.05 mm. The target region is selected by the operator by steering the projected spot to a vessel-free region of the optic nerve and physically moving or positioning the light collector at a region of the conjugate image field which corresponds to the illumination spot, and is also between or away from vessels.

The control/analysis module preferably includes a means for generating and accepting a medical information record database linkage, such as a program implemented in Windows and Visual Basic software, or other such software, that accepts entry of patient data via keyboard or network communication, and combines the patient data with the acquired spectra to form medical records. Preferably, it also accesses records for the same patient from storage to conveniently display and compare records, and may also include a number of threshold or simple diagnostic routines implemented as macros to highlight or annotate the transformed measurement traces it generates, and to print out the annotated data.

In a preferred embodiment, the control module is set to carry out signal acquisition for no more than a fixed number n of one-second intervals, and to terminate acquisition earlier if it has evaluated and positively approved a second, lesser fixed number m of well-formed signal traces, thus minimizing the period of direct observation of the patient's eye. The module generates audible prompts indicating the acquisition of proper traces, and indicating completion of the data acquisition, analysis or fitting steps. A printer may print out the transformed spectra and derived data with computer-generated or user-entered annotations.

BRIEF DESCRIPTION OF THE DRAWINGS

These and other features of the invention will be understood from the description herein in light of the ordinary knowledge of one skilled in the art, taken together with illustrative figures, wherein.

DETAILED DESCRIPTION

Figure 1:
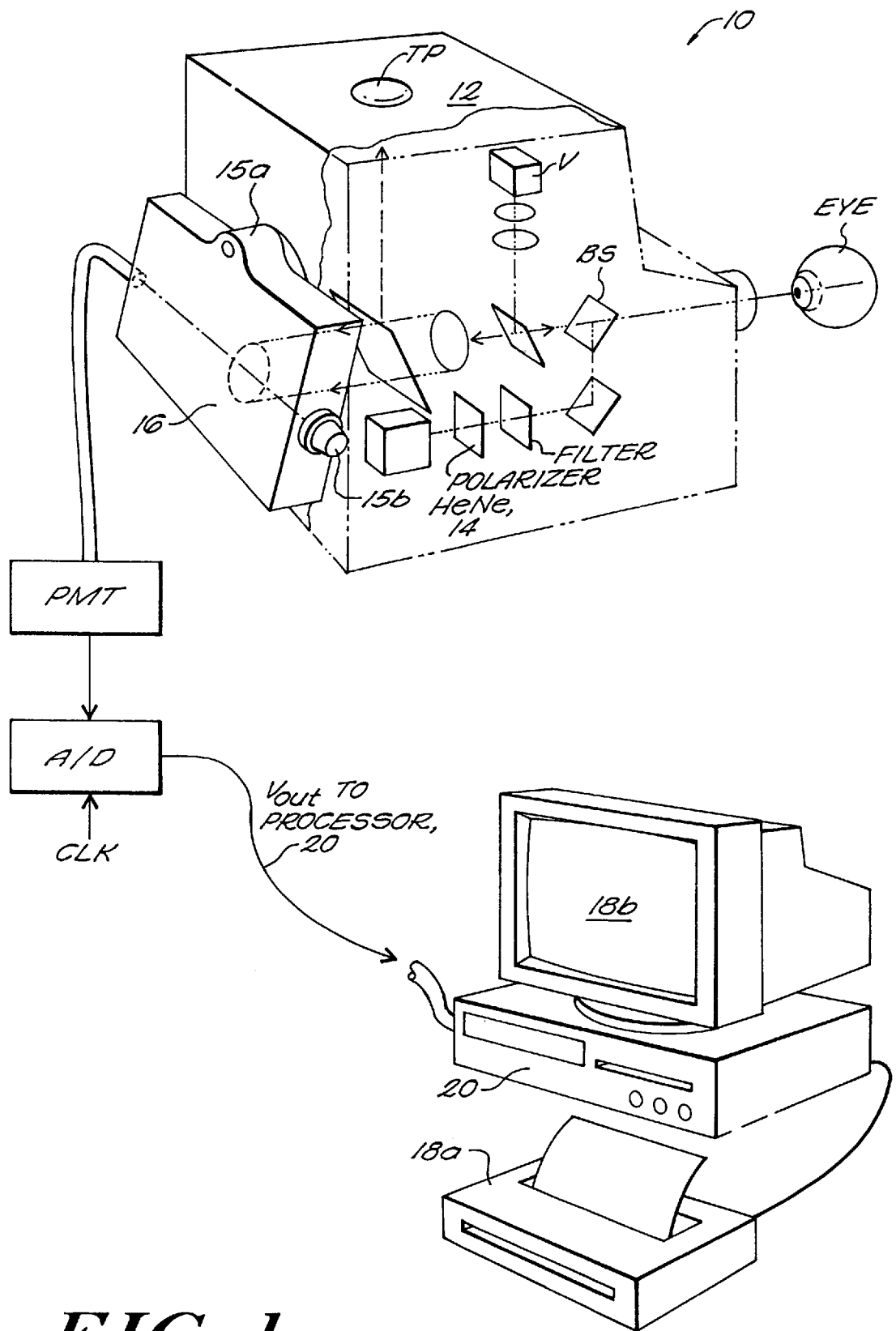
FIG. 1 shows a basic embodiment of the present invention.

FIG. 1 shows a basic embodiment 10 of the invention, which includes an ophthalmic imaging unit 12 which, for example, may include the basic steering system and imaging optics of a retinal camera. A laser source 14, illustratively a 633 nm HeNe laser, projects an illumination spot into the imaged field of the unit 12, and a detector assembly 16 is mounted on unit 12 to receive the light collected from the local area of tissue illuminated by the spot and convert it to an electrical signal. The photo-converted output of the detector passes to a control/processor unit 20 which in turn is connected to various output devices, illustratively a printer 18a and a display monitor 18b, as well as a sound generator user interface (not shown). The controller 20 may also control the state of the laser source 14, although in the prototype instrument a simple CW laser source was manually turned ON and OFF by the operator.

As described more fully below, the device is configured to provide an illumination and collection geometry that results in the detection of light that has undergone a suitably controlled tissue-bed scattering and randomization interaction along a path which introduces Doppler frequency shifts representative of the speed of capillary blood. The components 12, 14 and 16 are configured to rapidly and manually position these elements to create and to detect with discrimination the desired light signal, while the processor carries out tasks of partitioning the incoming electrical signal, evaluating the raw partitioned input, carrying out signal transformation and curve fitting operations to convert the Doppler distributions to capillary blood measurements, indicating status of the measurement protocol to the operator. It also constructs and stores medical records incorporating the acquired spectra and data.

In general terms, the present invention seeks both to reduce measurement error and variation, and to provide a process output that will serve as a dependable and repeatable measure of circulation in the head of the optic nerve, useful for clinical observation and baseline measurements, and susceptible to meaningful site-to-site and time-to-time comparisons as well as correlation with other parameters such as tissue thickness, blood flow, and the like. It projects at the head of the optic nerve an intense spot of laser light having a diameter which is preferably between about twenty and two hundred micrometers, causing tissue to glow diffusely from internally scattered light including light scattered by moving blood cells, and the device collects a representative portion of the light from an image of the illumination spot. This assures that the light which is collected has undergone the requisite degree of scattering and will have relatively stable signal to noise ratio and other characteristics. The collected light is sampled, undergoes a thresholding evaluation, and is Fourier transformed to produce a Doppler power spectrum or frequency histogram. The instrument next fits a curve and evaluates a low frequency shoulder of the spectrum, deriving a spreading parameter as the fundamental measure of the capillary blood particle speed. In various further steps of methods utilizing the present invention, this measure may be combined with another measurement, such as a reflectometry measurement, or with a protocol such as performing the measurement at a specific sequence of sites, to provide other useful clinical indications such as a change in the measurement parameter associated with cupping or other localized processes.

Figure 3A:
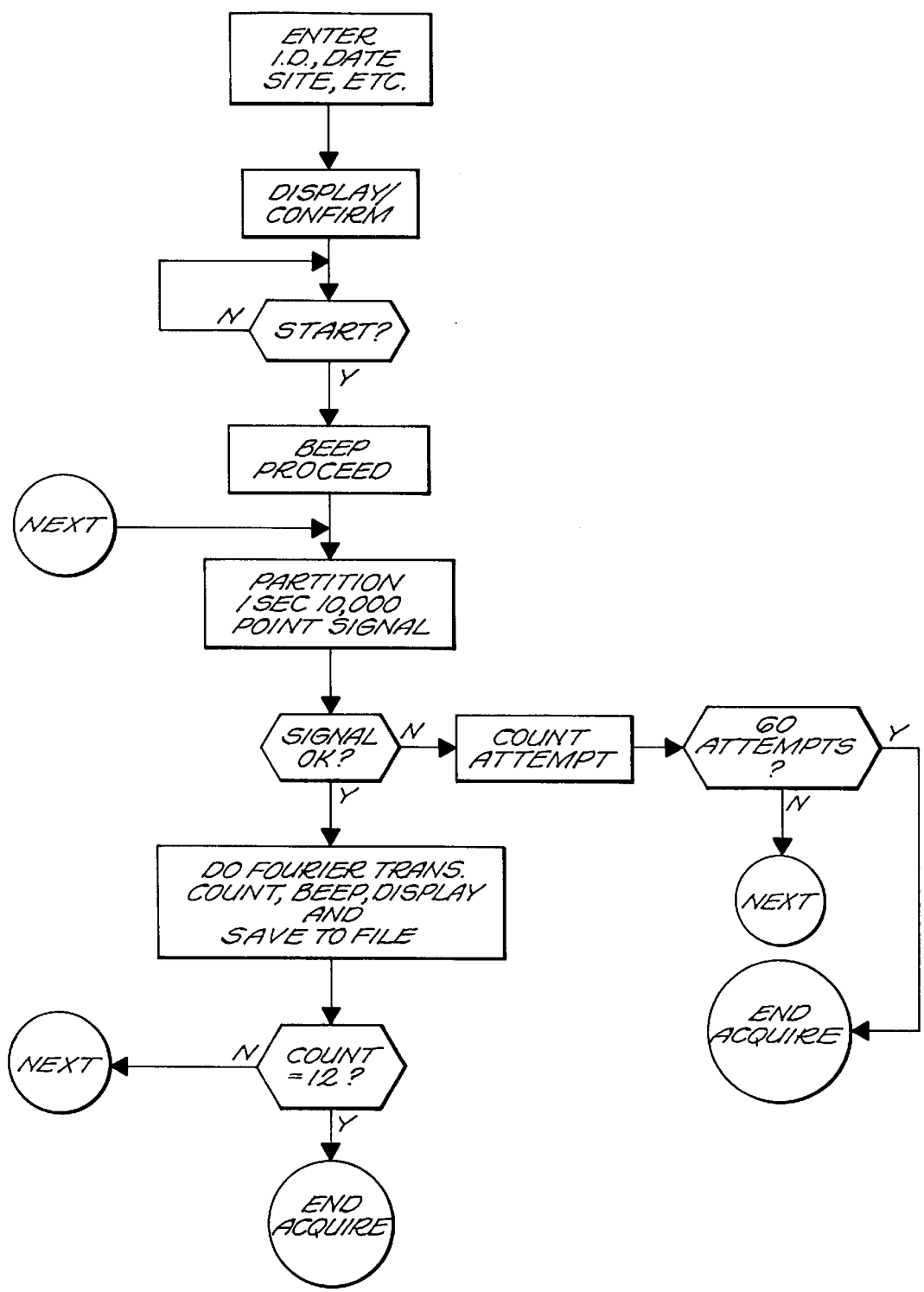
FIGS. 3A and 3B are flow charts showing operation of the control/analysis module of the embodiment of FIG. 1.
Figure 3B:
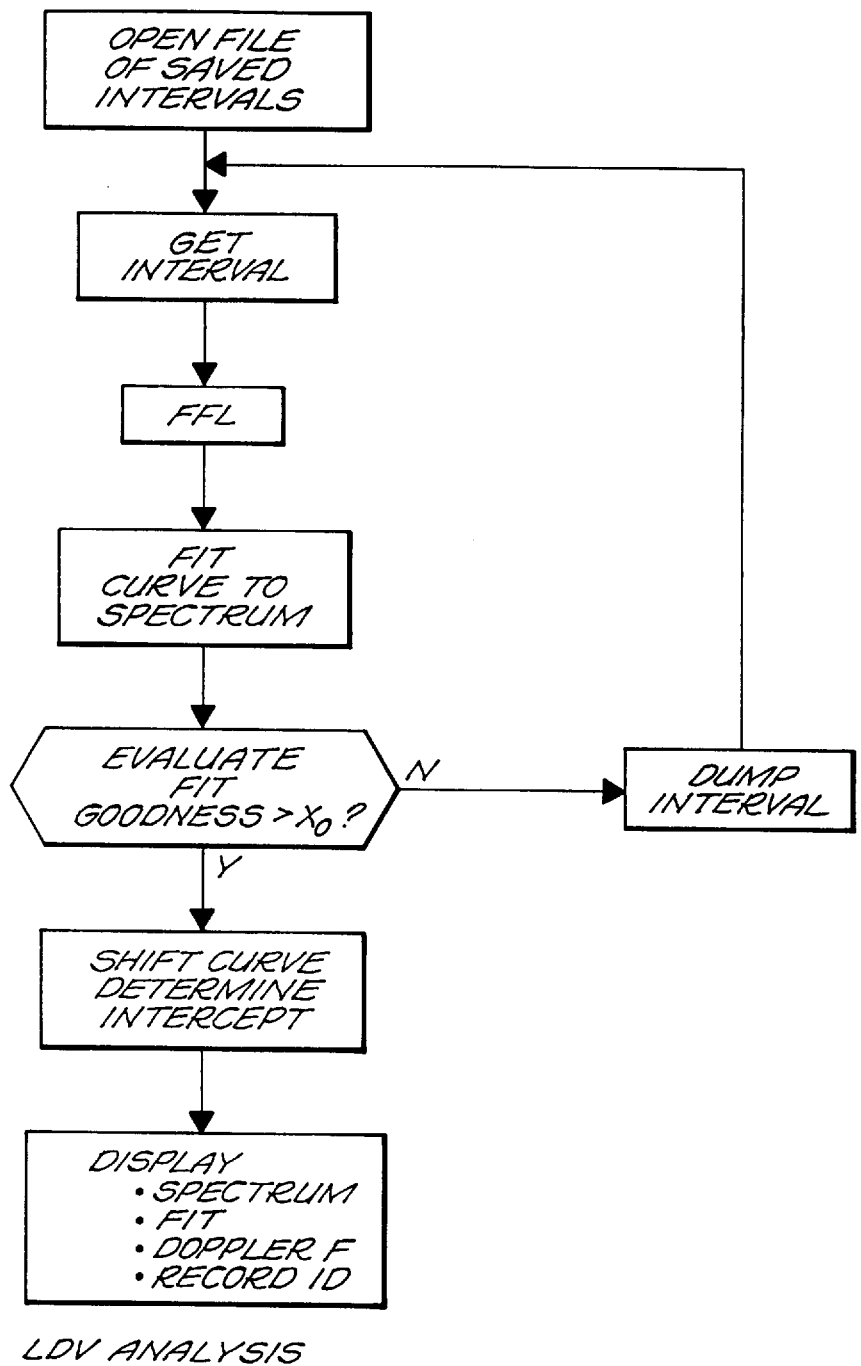

Operation of the device requires aiming by the operator, who first enters patient data, and who may further enter medical annotations and identification of sites. The device then carries out the acquisition of data, and to a large extent its analysis, automatically with the operation of two programs, LDV Acquire and LDV Analysis, both described below. The LDV Acquire program carries out operations on-line and in real time to assemble data files while the instrument and its operator interact directly with the patient. The laser may then be switched OFF while the LDV Analysis program carries out operations on the data files assembled in the first step. Operation flow charts for these two programs appear in FIGS. 3A and 3B.

As shown generally in FIG. 1, the laser source is coupled into the objective optical assembly by a beam splitter BS so that it passes through the front steering system (not illustrated) of the camera and enters the eye as a substantially collimated pencil, and therefore is brought to a point focus on the fundus, largely by the normal corneal and lens refractive focusing of the patients eye. For effecting the measurements as described below, the operator steers this point so that it falls on the head of the optic nerve surface. The detector unit 16 is mounted at the image plane of the retinal camera assembly 12, where it is rotatable around its bayonet mount 15a to provide an angular adjustment for orienting the detector along one dimension in the field of view. Control of a second dimension is provided by an adjustment knob 15b that moves a linear micrometer stage to provide radial positioning of the detector pick-up. In the prototype embodiment this light collector was the end of a 450 micrometer diameter optical fiber, positioned in the focal plane to collect light from the conjugate image of the fundus tissue. For a 35° field of view, this fiber face corresponds to a diameter of 150 micrometers on the fundus. The light collected in the fiber passes as the input to a photomultiplier tube PMT, which in turn has its output digitized by an analog-to-digit converter A/D operating at a sampling frequency set by a programmable clock signal CLK. In the prototype embodiment, the A/D unit was a comercially available sampler with a maximum sampling rate of 27 kHz, and was set to acquire ten thousand samples per second of the normalized photomultiplier output. This data stream was then fed to the processor 20 for signal analysis.

Figure 2:
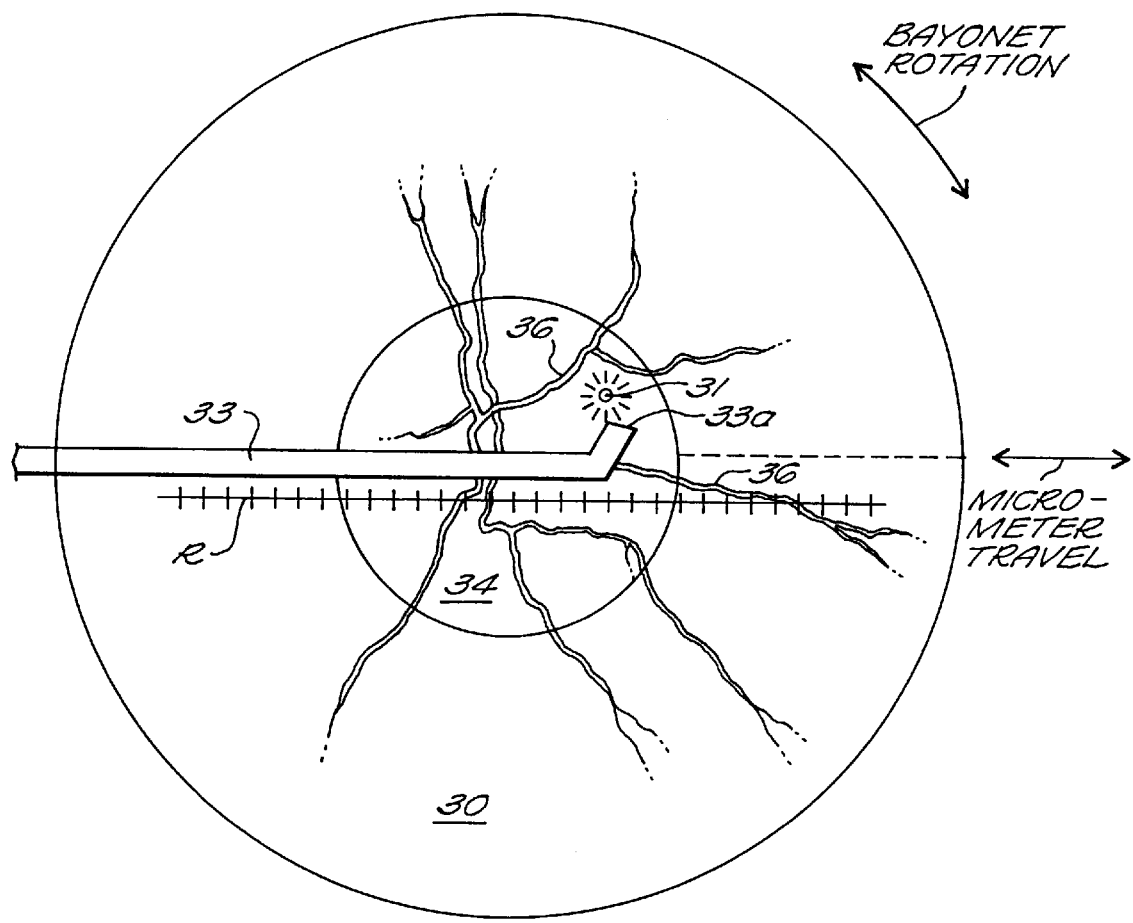
FIG. 2 is a observer's view of the operation of the embodiment of FIG. 1 for signal collection.

FIG. 2 shows a view through the observing eyepiece of the instrument, which for simplicity is shown as an eyepiece incorporated into a reflex-like prism viewing assembly on the housing of photodetector 16. As shown in FIG. 2, the instrument optics form an image of a fundus field 30 in the eyepiece, which is aimed by the operator so that the head 34 of the optic nerve appears as a bright disc in the field of view. The laser spot 31 is positioned by the operator in a region of the optic nerve head away from obvious vessels 36, and this position is preferably maintained, in a manner well understood in the art, by providing a fixation target (not shown) at which the patient gazes. An optical fiber pick-up is carried on the micrometer positioner along a linear path just ahead of or behind the focal plane, and both the fiber and its end face 33a are visible in the field of view as they move. As shown, the end of the fiber is hooked forward to aim the face 33a along the collection optical path. As indicated schematically in FIG. 2, the entire detector pick-up assembly also rotates, allowing r-θ positioning of the collection face 33a over an arbitrary point in the field, so that it is readily placed on the illuminated spot region, to collect scattered light returning from the tissue. Thus, light is collected from a fundus region having dimensions 1/M times those of the fiber, where M is the magnification as measured in the image plane, typically between about two and four magnifications, corresponding to fundus fields between about twenty and fifty degrees. A metric reticle R spans the field for estimating distances or sizes of features on the fundus.

In preferred implementations, the collection face 33a is sized to exactly or closely fit the spot size, and is positioned directly over or concentric with the illuminated spot when the neutral density filter is in position to allow focusing and alignment to be more conveniently carried out. The neutral density filter is then removed so that the eye is illuminated at the full permissible intensity and the collection output is sampled continuously. At this point, the signal acquisition program LDV Acquire is called, for example, by actuating a foot switch, causing the controller 20 to acquire and store suitable signal traces in the form of partitioned sampling intervals. The processor 20 operates under program control, emitting several different distinctive audible tones to report processing stages while the patient's eye is illuminated.

Figure 4A:
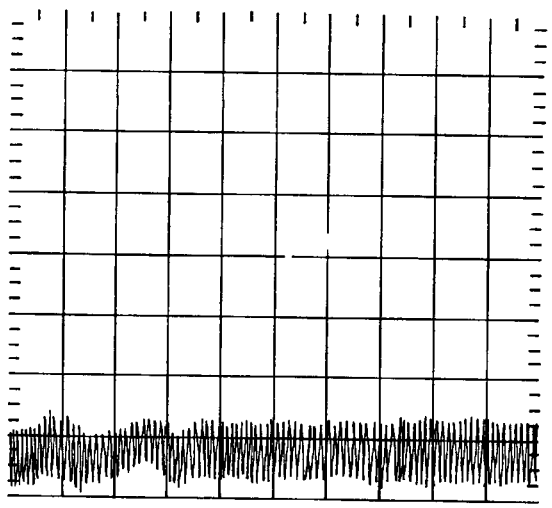
FIGS. 4A–4C show representative signal traces.
Figure 4B:
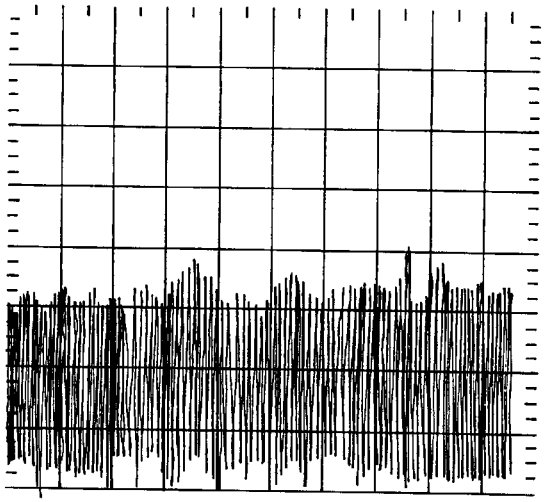
Figure 4C:
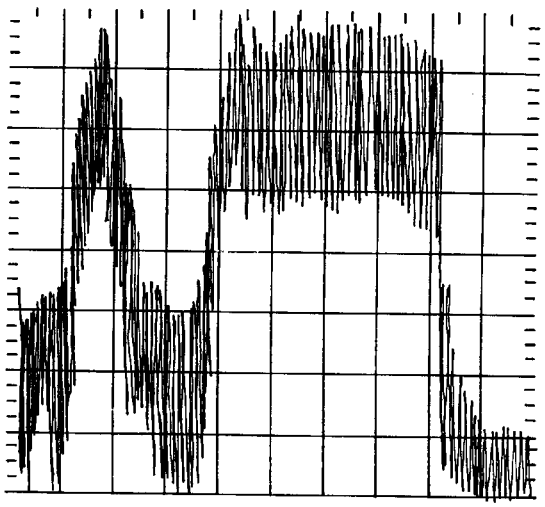

The LDV Acquire program operates as follows. Initially, identification information is entered and a file created with the patient's name, date, eye or measurement site and other information. The patient is provided with a fixation target, and the laser spot is aimed at the head of the optic nerve. When the user-operated foot switch provides a start pulse for initiation of the data acquisition, the processor emits a beep to confirm detection of the start pulse. It then proceeds to partition the incoming photomultiplier tube signal into one-second long, ten thousand point, digitized signals. Each raw one second interval is evaluated to assure that is sufficiently above the noise band to represent collected light, and that it is sufficiently free of fluctuation that the eye may be assumed to be stationary under the light spot. FIGS. 4A–4C show representative PMT signal records to illustrate this evaluation. The trace shown in FIG. 4A is homogeneous and of uniform, but low, amplitude, indicating simply detector noise (the background visible image light having been removed by a filter between the fiber and PMT). In this case, the laser may be OFF, the shutter or neutral density filter may be blocking the beam, the patient may have closed his eye lid, or the collector may be incorrectly positioned. FIG. 4B illustrates an acceptable detection signal, significantly above the noise threshold, and lying in a band of uniform amplitude. Such signals are counted as good signal sample intervals and saved for analysis. FIG. 4C by contrast shows a signal in which average amplitude jumps between two or more levels, indicating eye saccades or movement that brings either direct reflection from vessels or entirely different tissue regions below the spot and into the collector. These measurement intervals also are discarded. Thus only the intervals similar to that of FIG. 4B pass the initial signal evaluation tests and are saved as data files; a count of the good intervals is maintained, while bad intervals are discarded. As each good interval passes this evaluation, a fast Fourier transform is performed to generate a graphic spectrum, and this spectrum is displayed on the monitor screen so the operator can briefly assess its shape or distribution. A running count of the number of samples evaluated ("Attempts") and of the number of good sample intervals which are saved ("Acquired data sets") is displayed, and the processor emits an audible beep each time an interval is saved.

After a preset number of samples has been saved, the processor emits a different, end-of-acquisition, signal or beep to alert the operator that data acquisition has been completed. At this point the laser may be shut down and the patient may move. If less than the desired number of good sample intervals have been obtained in sixty one-second attempts, the processor emits the same completion-of-measurement sound, and analysis simply proceeds with those good samples that were obtained. In the prototype device, acquisition continues until twelve good samples, or sixty attempts, occur. The good samples constitute the file upon which analysis is undertaken.

Following patient data acquisition, the LDV Analysis program is called, and the file consisting of saved samples is identified and opened. The analysis program performs a fast Fourier transform on each one second data interval and graphs a five thousand point power spectrum on the range 0–5 kHz. As noted above, the instrument aims a spot at tissue and collects light over a region of substantially the same size centered on the spot to assure first that the collected light always undergoes a substantially similar interaction with the targeted tissue, and second that the amplitude of the collected light, and the signal to noise ratio of the relevant components, is fairly stable. In general, once the photoconverted signal has been transformed, very small frequency shifts, below about 50 Hz occurring in the Doppler spectrum may be ascribed to slow movements of the illuminated tissue, while high frequency shifts above several kiloherz may arise from several causes, including vascular blood flow, faster tissue movements, and a low amplitude noise component. The LDV Analysis program analyzes the mid-range shifts present in the Doppler spectrum to provide both a graph and a single-number output quantifying capillary blood speed.

Figure 5:
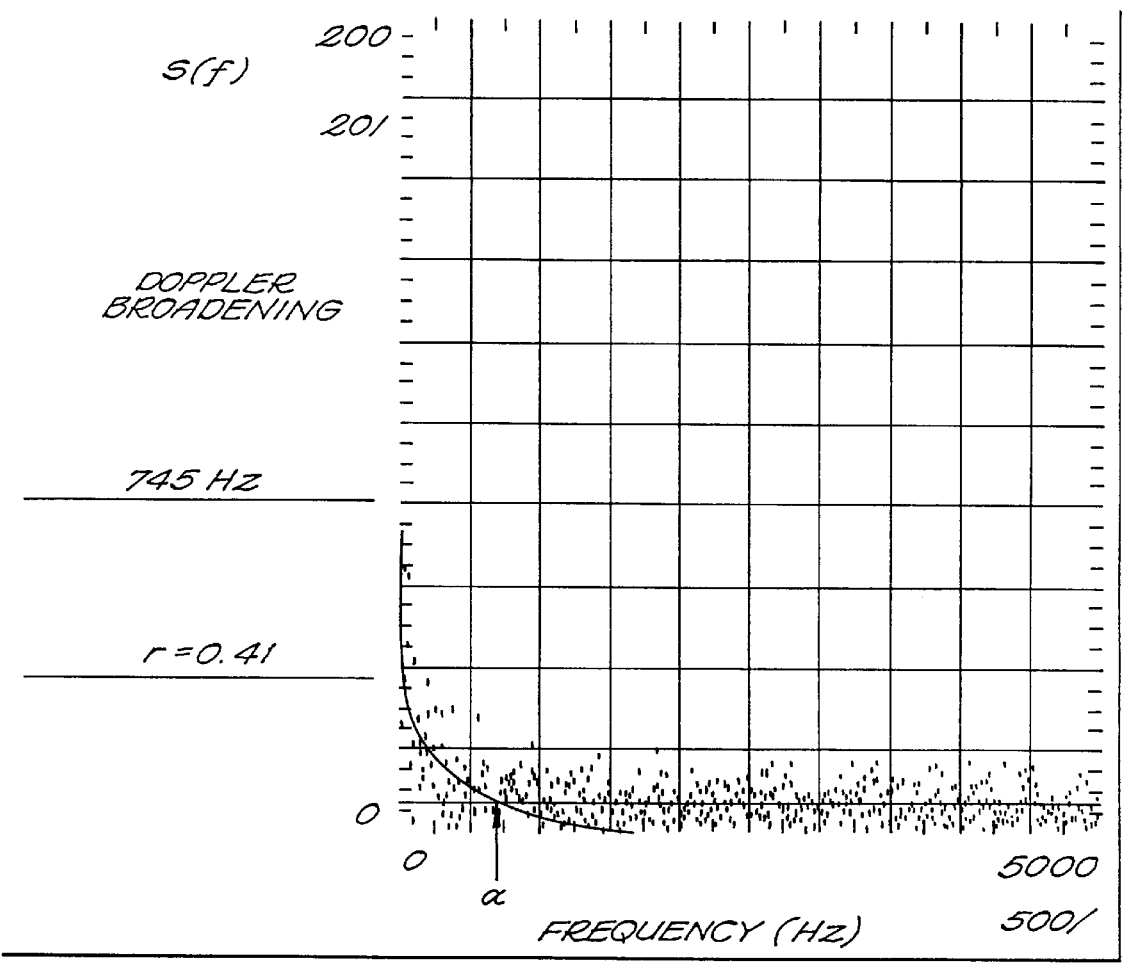
FIG. 5 shows a representative trace after transformation by the control-analysis module.
Figure 6A:
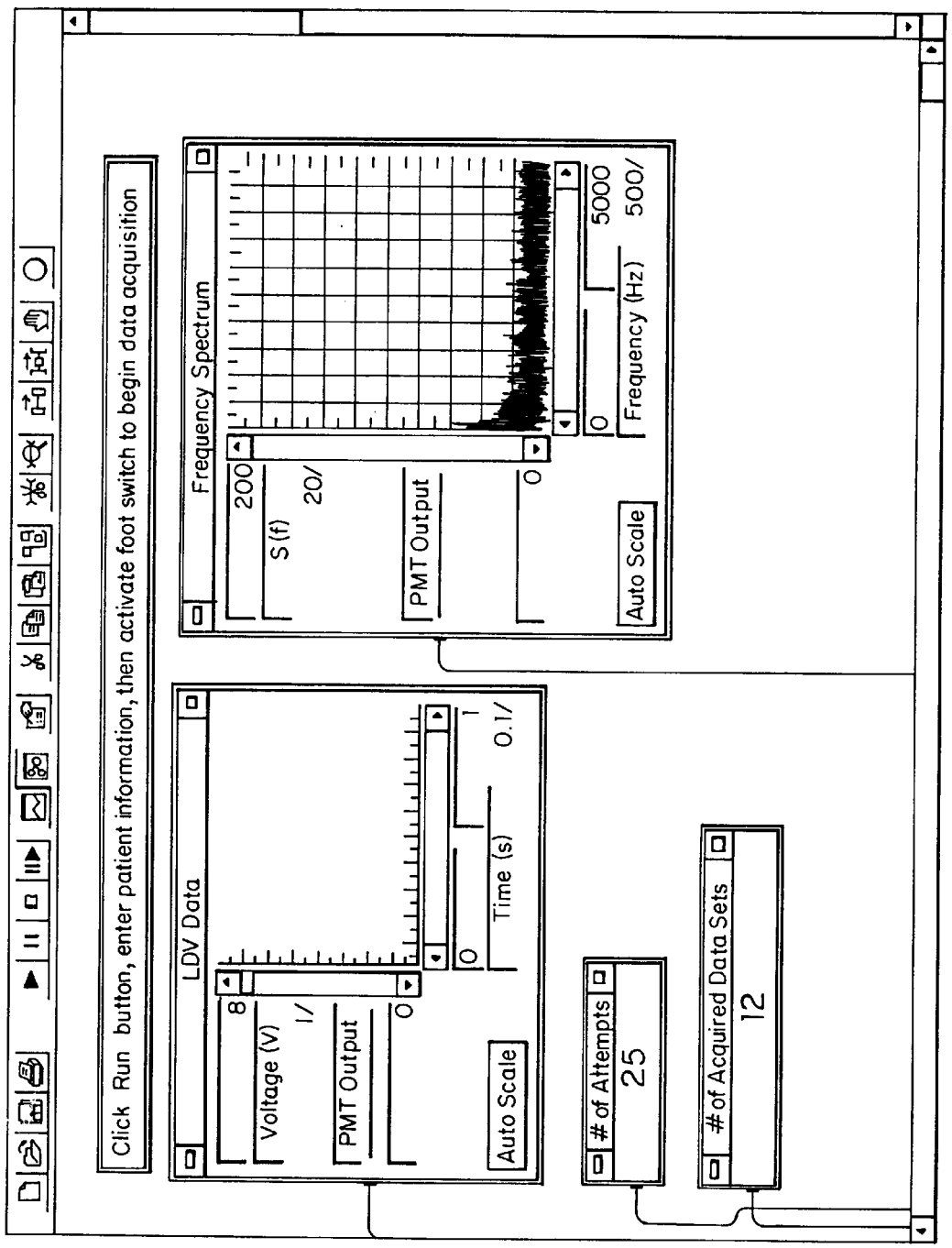
FIGS. 6A and 6B show module screen displays during acquisition and analysis stages of operation, respectively, of the embodiment of FIG. 1.
Figure 6B:
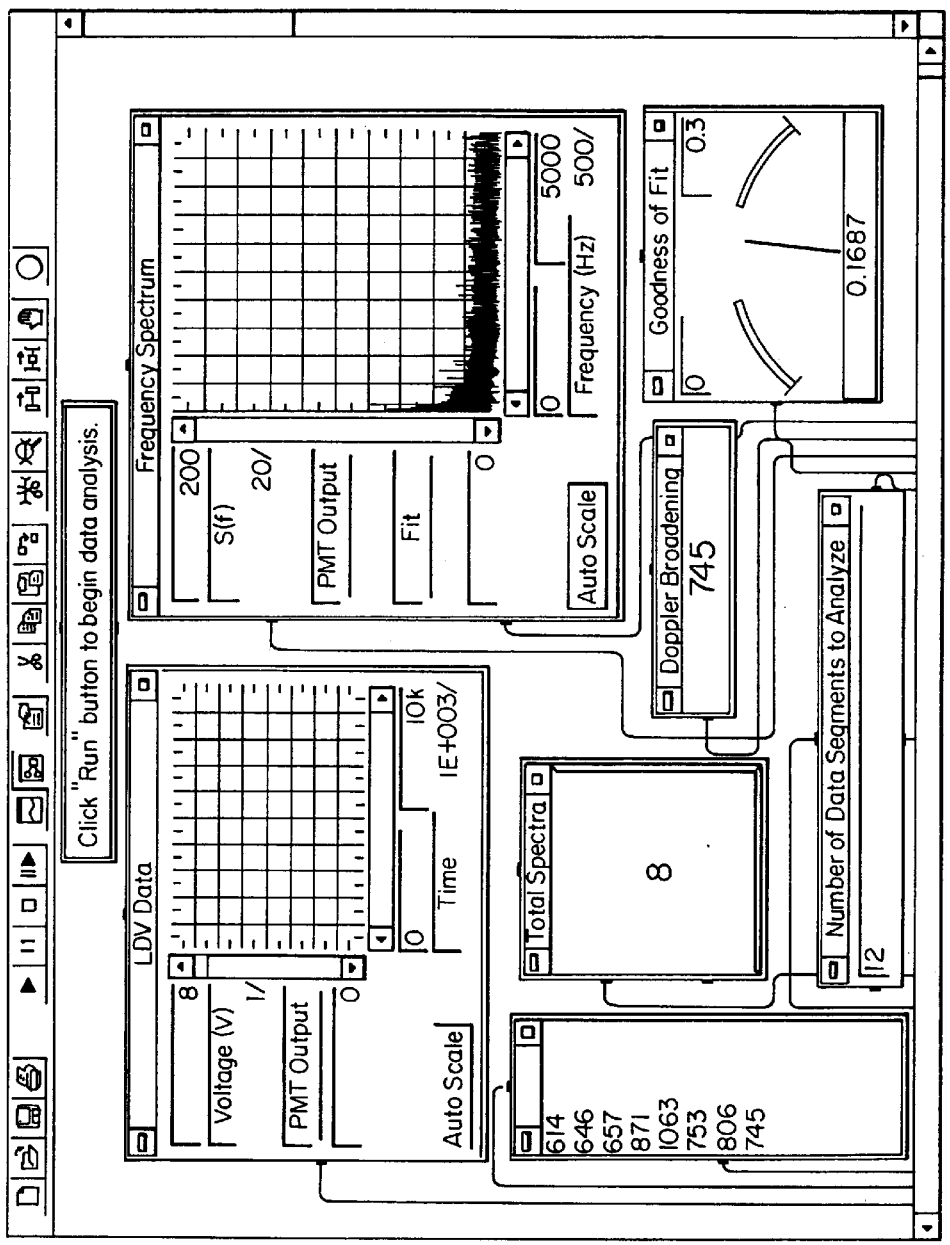

First, the LDV Analysis program fits a continuous log divergence function to the mid-range portion of the Doppler spectrum between a lower cut-off of one hundred Hz and an upper cut-off of five to seven hundred Hz, which is dominated by single-scattering event interactions with capillary blood. Both the points of the spectrum and its fitted curve are displayed. The zero-amplitude or baseline noise value is set at the level of the high frequency asymptote of the transformed frequency spectrum. The zero amplitude intercept of the fitted curve, which is the Doppler broadening parameter $\alpha$ of the Stern and Lappe calculation, is taken as equal, modulo a constant of proportionality, to the capillary blood speed. A "goodness of fit" parameter is also calculated for the spectrum by applying a least squares measure of closeness to the plotted frequency points. That is, the distance of each point from the curve is squared, and the results are summed to determine how well the graphed curve fits the points of the transformed signal interval. If the goodness parameter exceeds a preset threshold value, then the spectrum and its superimposed curve are automatically printed out. If the fit does not exceed this threshold, the result is discarded and the next signal interval is loaded from the file, and the spectrum for the next interval is evaluated in the same way. The Doppler broadening value $\alpha$, a measure of the width of the spectrum, is printed out with each of the good spectra, as shown below in FIGS. 5 and 6B. The display screen also identifies the number of acceptable spectra and the total number of spectra available for analsis as provided by LDV Acquire, as well identifying the specific record being processed or displayed.

In the above-described prototype embodiment of the invention, the laser source 14 is a one-half milliwatt HeNe laser with a polarized output. A rotating polarizer in the beam path adjusts the intensity to a biologically safe power level, and a ten percent neutral density filter is removably fitted in-line to further reduce the intensity and permit the operator to conveniently aim and align the system for extended times without discomforting the patient. The wavelength $\lambda$ of 633 mn propagates well in tissue, having a 1/e attenuation depth of about one half a millimeter. As shown in FIG. 1, the laser is coupled by a beam splitter BS into the normal ophthalmic viewing device 12, which in the prototype embodiment was a Topcon TRC-50X retinal camera. The camera had a rotatable bayonet mount ahead of its image plane for receiving a 35 mm camera back, and the detector 16 was configured to attach to the bayonet and position the face of an optical fiber in an image plane position to selectively collect light.

In the Topcon instrument, the system source of visible observation light denoted by source V is configured to enter the eye and illuminate the fundus through an annular pupil, and the laser spot is coupled in through the same aperture. Return image light is collected through the center of the annulus, so the light scattered by tissue from the spot illumination appears in the camera image plane. This on-axis collection geometry with concentric annular illumination eliminates corneal surface reflections from the image. The instrument may include additional light sources or filters, for example to provide red-free observation light during set-up so that the spot/collection may be more effectively positioned to avoid vascular scattering and receive only the desired "isotropic" capillary light scatter signal.

Preferably the viewing instrument is also provided with a film imaging port, such as the port designated TP in FIG. 1, at which a camera back, such as a Polaroid or CCD imaging back is attached to make an immediate image of the probed site, wherein the illumination spot directly appears on the captured image. If a CCD imager is employed, the graphic information developed by the LDV Analysis program may be directly linked to or graphically overlaid upon or displayed within a window of the acquired image.

As described above, the prototype embodiment utilized a spot of approximately 150 micrometers diameter and a collection fiber having the same effective diameter in the fundus plane. More generally, the invention contemplates that collection apertures (or fiber ends) having different effective diameters may be employed for taking more localized measurements of capillary bed blood speed. In particular a diameter of between about twenty and fifty micrometers may be employed to select return light from a small subregion of the optic nerve head, and thus usefully probe dimples or monitor sites of progressive thinning or atrophy. Furthermore, multiple different fibers may be mounted on several different micrometer positioners in the detector assembly, and each moved along a different X-, Y- or oblique axis, thereby allowing the operator to selectively position a collection aperture of the desired size over the site of interest. In each case the collector is preferably centered on the illumination spot to provide an fixed interaction condition for all collection sites. Thus, in accordance with various methods of the present invention, the operator may perform Doppler broadening measurements at sites situated on a path across the optic nerve head, on a plurality of sites proximate to the edge or the center, or at specific sites at which tissue changes have been observed.

The invention being thus disclosed and a representative embodiments of the apparatus and its methods of use illustrated, further variations and modifications thereof will occur to those skilled in the art, and all such variations and modifications are considered to be within the scope of the invention as set forth in the claims appended hereto.

What is claimed is:

1. A tissue examination system comprising
   an ophthalmic viewing and imaging device having an objective optical assembly configured for imaging an object plate at the fundus of an eye and having a focal plane at which an image of the fundus is formed
   a laser input source coupled to said device for directing a laser beam to illuminate a spot on the fundus
   a photodetector assembly comprising a photoconversion unit for converting a light signal to an electrical signal, and a collector unit having a collection aperture of defined size for collecting light and conveying collected light to the photoconversion unit for forming the electrical signal
   a processor/control module connected to receive the electrical signal and transform it to a Doppler frequency distribution, and
   a manually operable positioning assembly for moving the collection aperture in said focal plane to position the collection aperture to selectively collect light diffusely scattered from a substantially homogeneous bed of tissue under the laser spot
   said processor/control module being operative to automatically collect and evaluate a plurality of raw signal intervals as said collected light is converted, and to process evaluated signals and form a measure of capillary blood speed in the fundus tissue illuminated by the laser spot.

2. A tissue examination system according to claim 1, wherein the collection aperture is an end of an optical fiber.

3. A tissue examination system according to claim 2, wherein the collection aperture has an effective diameter under approximately two hundred micrometers at the object plane.

4. A tissue examination system according to claim 3, wherein the end of the optical fiber has a size effective to selectively collect diffusely scattered light from a substantially homogeneous tissue region between vessels on the optic nerve of an eye.

5. A tissue examination system according to claim 1, wherein said processor/control module provides an audible signal as it determines a positive evaluation of a raw signal interval.

6. A tissue examination system according to claim 5, wherein the processor/control module includes data base software for receiving patient data input information and operates to link said information to processed Doppler distributions and thereby form a medical record including graphic data.

7. A tissue examination system according to claim 3, wherein said aperture has an effective diameter of about twenty to about fifty micrometers at the object plane.

8. A tissue examination system comprising
   an ophthalmic viewing and imaging device having an objective optical assembly configured for imaging an object plane at the fundus of an eye and having a focal plane at which an image of the fundus is formed
   a laser input source coupled to said device for directing a laser beam to illuminate a spot on the fundus
   a photodetector assembly comprising a photoconversion unit for converting a light signal to an electrical signal, and a collector unit including an optical fiber for collecting light, the fiber having an end defining a collection aperture of defined size of less than about 200 micrometers at the object plane for collecting and conveying collected light to the photoconversion unit for forming the electrical signal
   a processor/control module connected to receive the electrical signal and transform it to a Doppler frequency distribution, and
   a manually operable positioning assembly for moving the end of the fiber in said focal plane to selectively collect light diffusely scattered from tissue under the laser spot
   said processor/control module being operative to automatically collect and evaluate a plurality of raw signal intervals as said collected light is converted, and to process evaluated signals and form a measure of capillary blood speed in the fundus tissue illuminated by the laser spot,
wherein said processor/control module is operative to collect said raw signals during a first time period having a preset maximum duration while reporting adequacy of signals evaluated in said first time period, and thereafter process at least a portion of the signals collected in the first time period, thereby reducing patient discomfort.

9. A tissue examination system according to claim 8, wherein the processor/control module operates to acquire a first plurality of m representative raw signal intervals during the process of evaluating no more than a second plurality of n sample intervals.

10. A tissue examination system according to claim 9, wherein the processor/control module operates to form records fitting a log divergence to transformed frequency spectra of the signal intervals and identify the Doppler broadening parameter characteristic of capillary blood speed.

11. A tissue examination system comprising
    an ophthalmic viewing and imaging device having an objective optical assembly configured for focally imaging the fundus of an eye and having a focal plane at which an image of the fundus is formed
    a laser input source directed by said objective optical assembly to form a laser spot on the head of the optic nerve, the laser spot having a characteristic dimension permitting placement entirely within a capillary region
    a photodetector assembly comprising a collector unit having a collection aperture of defined size for collecting light and a photoconversion unit for converting collected light to an electrical signal, said collector unit being coupled for conveying collected light to the photoconversion unit to form the electrical signal a processor/control module connected to receive the electrical signal, and means for placing the collection aperture substantially concentrically over the laser spot on the head of the optic nerve to collect a sample of light scattered from a homogeneous tissue bed and having stable and repeatable Doppler interaction characteristics said processor/control module being operative to partition and evaluate a plurality of raw signal intervals as said light is collected, transforming the evaluated signals to a frequency distribution and processing the distribution to determine and print out its Doppler broadening parameter and thereby record capillary blood speed as the device is aimed at the fundus.

12. A method of evaluating tissue of the head of the optic nerve in an eye, such method comprising the steps of directing at the eye fundus an ophthalmic viewing and imaging device having an objective optical assembly configured for focally imaging the fundus and forming an image thereof in a focal plane directing a laser input source via said objective optical assembly to an illumination spot on the head of the optic nerve and entirely within a capillary region detecting light diffusely scattered in a homogeneous tissue bed at the spot by a photodetector assembly comprising a collector unit having a collection aperture of defined size for collecting light and a photoconversion unit for converting collected light to an electrical signal, wherein the collector unit is coupled for conveying collected light to the photoconversion unit to form the electrical signal, and processing the electrical signal, wherein the step of detecting includes placing the collection aperture in the image plane substantially concentrically over the laser spot to collect a sample of light which has undergone multiple scattering interactions in the tissue bed and has stable and repeatable Doppler interaction characteristics with optic nerve tissue and the processing automatically partitions and evaluates a plurality of raw signal intervals as said light is collected, transforming the evaluated signals to a frequency distribution and processing the distribution to determine and print out its Doppler broadening parameter and thereby record capillary blood speed as the device is aimed at the fundus.

* * * * *